United States Patent
Shimomura

(10) Patent No.: US 12,320,929 B2
(45) Date of Patent: Jun. 3, 2025

(54) ULTRASOUND DIAGNOSTIC APPARATUS AND CONTROL METHOD FOR ULTRASOUND DIAGNOSTIC APPARATUS

(71) Applicant: FUJIFILM Corporation, Tokyo (JP)

(72) Inventor: Koji Shimomura, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 145 days.

(21) Appl. No.: 18/176,679

(22) Filed: Mar. 1, 2023

(65) Prior Publication Data

US 2023/0314581 A1 Oct. 5, 2023

(30) Foreign Application Priority Data

Mar. 30, 2022 (JP) .................. 2022-055420

(51) Int. Cl.
*G01S 7/52* (2006.01)
*A61B 8/00* (2006.01)
*A61B 8/08* (2006.01)

(52) U.S. Cl.
CPC ........ *G01S 7/52096* (2013.01); *A61B 8/4488* (2013.01); *A61B 8/467* (2013.01); *A61B 8/5215* (2013.01); *A61B 8/56* (2013.01); *G01S 7/52084* (2013.01)

(58) Field of Classification Search
CPC ............. G01S 7/52096; G01S 7/52084; A61B 8/4488; A61B 8/467; A61B 8/5215; A61B 8/56; A61B 8/5207; A61B 8/54
See application file for complete search history.

(56) References Cited

U.S. PATENT DOCUMENTS

| | | | |
|---|---|---|---|
| 2013/0072800 A1* | 3/2013 | Lee ........................ | A61B 8/56 600/447 |
| 2014/0379212 A1* | 12/2014 | Min ...................... | B60K 35/00 715/834 |
| 2021/0106305 A1* | 4/2021 | Wang ..................... | A61B 8/466 |
| 2021/0223375 A1* | 7/2021 | Imai .................... | G01S 15/8911 |
| 2023/0165569 A1* | 6/2023 | Sonnenschein ........ | G16H 40/67 600/437 |

FOREIGN PATENT DOCUMENTS

JP 2021-529030 A 10/2021
WO WO-2009065167 A1 * 5/2009 ............... A61B 8/00

* cited by examiner

*Primary Examiner* — Alexei Bykhovski
(74) *Attorney, Agent, or Firm* — Studebaker Brackett PLLC

(57) ABSTRACT

Provided are an ultrasound diagnostic apparatus and a control method for an ultrasound diagnostic apparatus capable of reducing power consumption by reliably detecting an operation status without being bothered by unintended vibration, contact, or the like.
A power saving control circuit controls operations of an ultrasound probe and an apparatus main body by selecting one of a normal mode in which the ultrasound probe and the apparatus main body are normally operated or a power saving mode in which power consumption of at least a part of the ultrasound probe and the apparatus main body is reduced, on the basis of a determination result of the probe use determination unit as to whether or not the ultrasound probe is being used and presence or absence of an operation of the operation panel detected by the touch sensor.

13 Claims, 10 Drawing Sheets

ULTRASOUND DIAGNOSTIC APPARATUS AND CONTROL METHOD FOR ULTRASOUND DIAGNOSTIC APPARATUS

CROSS-REFERENCE TO RELATED APPLICATIONS

The present application claims priority under 35 U.S.C. § 119 to Japanese Patent Application No. 2022-055420, filed on Mar. 30, 2022. The above application is hereby expressly incorporated by reference, in its entirety, into the present application.

BACKGROUND OF THE INVENTION

1. Field of the Invention

The present invention relates to an ultrasound diagnostic apparatus and a control method for an ultrasound diagnostic apparatus, and more particularly relates to a reduction in power consumption of an ultrasound diagnostic apparatus provided with an ultrasound probe and an apparatus main body.

2. Description of the Related Art

Hitherto, an ultrasound diagnostic apparatus using an ultrasound image has been put to practical use in a medical field. In general, an ultrasound diagnostic apparatus of this type comprises an ultrasound probe incorporating an oscillator array, and an apparatus main body connected to the ultrasound probe, and an ultrasound beam is transmitted from the oscillator array of the ultrasound probe toward a subject, an ultrasound echo from the subject is received by the oscillator array, and a reception signal is electrically processed so that an ultrasound image is generated, and the generated ultrasound image is displayed on a monitor of the apparatus main body.

In recent years, an ultrasound diagnostic apparatus has been developed in which operability and maneuverability of an ultrasound probe are improved by connecting the ultrasound probe and an apparatus main body through wireless communication.

In such an ultrasound diagnostic apparatus, generally, a battery is incorporated in the ultrasound probe, and the ultrasound probe is operated by power from the battery. In addition, an ultrasound diagnostic apparatus, such as a so-called laptop type and cart type, is operated by power from a battery incorporated in the apparatus main body in many cases. Therefore, in order to enable the operation for a long period of time, a reduction in power consumption of the ultrasound diagnostic apparatus has been requested.

For example, JP2021-529030A discloses an ultrasound diagnostic apparatus that detects an operation status of an ultrasound probe by using a motion sensor mounted in the ultrasound probe and that shifts to a low power state on the basis of a detection result thereof. With this ultrasound diagnostic apparatus, it is possible to reduce power consumption because the motion sensor detects that the ultrasound probe is not moving and a power state is switched to the low power state instead of the current power state.

SUMMARY OF THE INVENTION

However, in a case in which the power state is switched by detecting the operation status of the ultrasound probe with the motion sensor mounted in the ultrasound probe, there is a concern in that the power state may be switched from the low power state to a normal power state by erroneous detection of the motion sensor that the ultrasound probe is being operated even though the ultrasound probe is not actually being operated, for example, in a case in which a work table or the like on which the ultrasound probe is placed vibrates for some reason or a case in which a user comes into contact with the ultrasound probe accidentally. Such erroneous detection of the motion sensor hinders the reduction in power consumption.

The present invention has been made in order to solve such a conventional problem, and an object of the present invention is to provide an ultrasound diagnostic apparatus and a control method for an ultrasound diagnostic apparatus capable of reducing power consumption by reliably detecting an operation status without being bothered by unintended vibration, contact, or the like.

In order to achieve the above object, according to the present invention,
there is provided an ultrasound diagnostic apparatus provided with an ultrasound probe having an oscillator array, and an apparatus main body connected to the ultrasound probe, the ultrasound diagnostic apparatus comprising:
an imaging unit that transmits and receives an ultrasound beam to and from a subject through the oscillator array and generates an ultrasound image on the basis of a reception signal output from the oscillator array;
a probe use determination unit that analyzes the ultrasound image to determine whether or not the ultrasound probe is being used;
an operation panel in which a touch sensor is mounted; and
a power saving control circuit that controls operations of the ultrasound probe and the apparatus main body by selecting one of a normal mode in which the ultrasound probe and the apparatus main body are normally operated or a power saving mode in which power consumption of at least a part of the ultrasound probe and the apparatus main body is reduced, on the basis of a determination result of the probe use determination unit as to whether or not the ultrasound probe is being used and presence or absence of an operation of the operation panel detected by the touch sensor.

It is preferable that the probe use determination unit determines that the ultrasound probe is being used in a case in which the ultrasound image shows that jelly is applied to the ultrasound probe or that the ultrasound probe is not in a midair radiation state, and determines that the ultrasound probe is not being used in a case in which the ultrasound image shows that jelly is not applied to the ultrasound probe and that the ultrasound probe is in the midair radiation state.

The power saving control circuit may switch the normal mode to the power saving mode in a case in which the probe use determination unit determines that the ultrasound probe is not being used and the touch sensor detects that the operation panel is not being operated for a predetermined time in the normal mode.

Further, the power saving control circuit may switch the power saving mode to the normal mode in a case in which the touch sensor detects that the operation panel is being operated in the power saving mode.

The ultrasound probe may have a probe sensor which detects that the ultrasound probe is gripped by a user, and the power saving control circuit may be configured to switch the power saving mode to the normal mode in a case in which the probe sensor detects that the ultrasound probe is gripped in the power saving mode.

It is preferable that the probe sensor consists of at least one of a pressure sensor, a capacitance sensor, or a temperature sensor mounted in the ultrasound probe.

It is preferable that the power saving mode includes a first mode in which only power consumption in the imaging unit, in the ultrasound probe and the apparatus main body, is reduced and a second mode in which overall power consumption of the ultrasound probe and the apparatus main body is reduced.

The power saving control circuit may reduce the power consumption of the imaging unit by selecting the first mode in a case in which the probe use determination unit determines that the ultrasound probe is not being used for a predetermined first time.

Further, the power saving control circuit may also reduce the overall power consumption of the ultrasound probe and the apparatus main body by switching the first mode to the second mode in a case in which the touch sensor detects that the operation panel is not being operated for a predetermined second time in the first mode.

It is preferable that the operation panel has a monitor and the touch sensor disposed so as to overlap the monitor.

The power saving control circuit may also be configured to switch the power saving mode to the normal mode in a case in which the touch sensor detects that the operation panel is brought into contact in a predetermined first contact pattern in the power saving mode.

Further, the power saving control circuit may also switch the normal mode to the power saving mode in a case in which the touch sensor detects that the operation panel is brought into contact in a predetermined second contact pattern in the normal mode.

In this case, the first contact pattern and the second contact pattern may be the same patterns as each other.

According to the present invention,
there is provided a control method for an ultrasound diagnostic apparatus provided with an ultrasound probe having an oscillator array, and an apparatus main body connected to the ultrasound probe, the control method comprising:
transmitting and receiving an ultrasound beam to and from a subject through the oscillator array and generating an ultrasound image on the basis of a reception signal output from the oscillator array;
analyzing the ultrasound image to determine whether or not the ultrasound probe is being used;
detecting presence or absence of an operation of an operation panel with a touch sensor; and
controlling operations of the ultrasound probe and the apparatus main body by selecting one of a normal mode in which the ultrasound probe and the apparatus main body are normally operated or a power saving mode in which power consumption of at least a part of the ultrasound probe and the apparatus main body is reduced, on the basis of a determination result as to whether or not the ultrasound probe is being used and the presence or absence of the detected operation of the operation panel.

According to the present invention, the power saving control circuit controls the operations of the ultrasound probe and the apparatus main body by selecting one of the normal mode in which the ultrasound probe and the apparatus main body are normally operated or the power saving mode in which power consumption of at least a part of the ultrasound probe and the apparatus main body is reduced, on the basis of the determination result of the probe use determination unit as to whether or not the ultrasound probe is being used and the presence or absence of the operation of the operation panel detected by the touch sensor, so that it is possible to reduce power consumption by reliably detecting the operation status without being bothered by unintended vibration, contact, or the like.

DESCRIPTION OF THE PREFERRED EMBODIMENTS

Hereinafter, embodiments of the present invention will be described with reference to the accompanying drawings.

The following description of constitutional requirements is based on a representative embodiment of the present invention, but the present invention is not limited to such an embodiment.

In the present specification, a numerical range represented by "to" means a range including numerical values before and after "to" as a lower limit value and an upper limit value.

In the present specification, "same" and "equal" include an error range generally allowed in the technical field.

Embodiment 1

Figure 1:
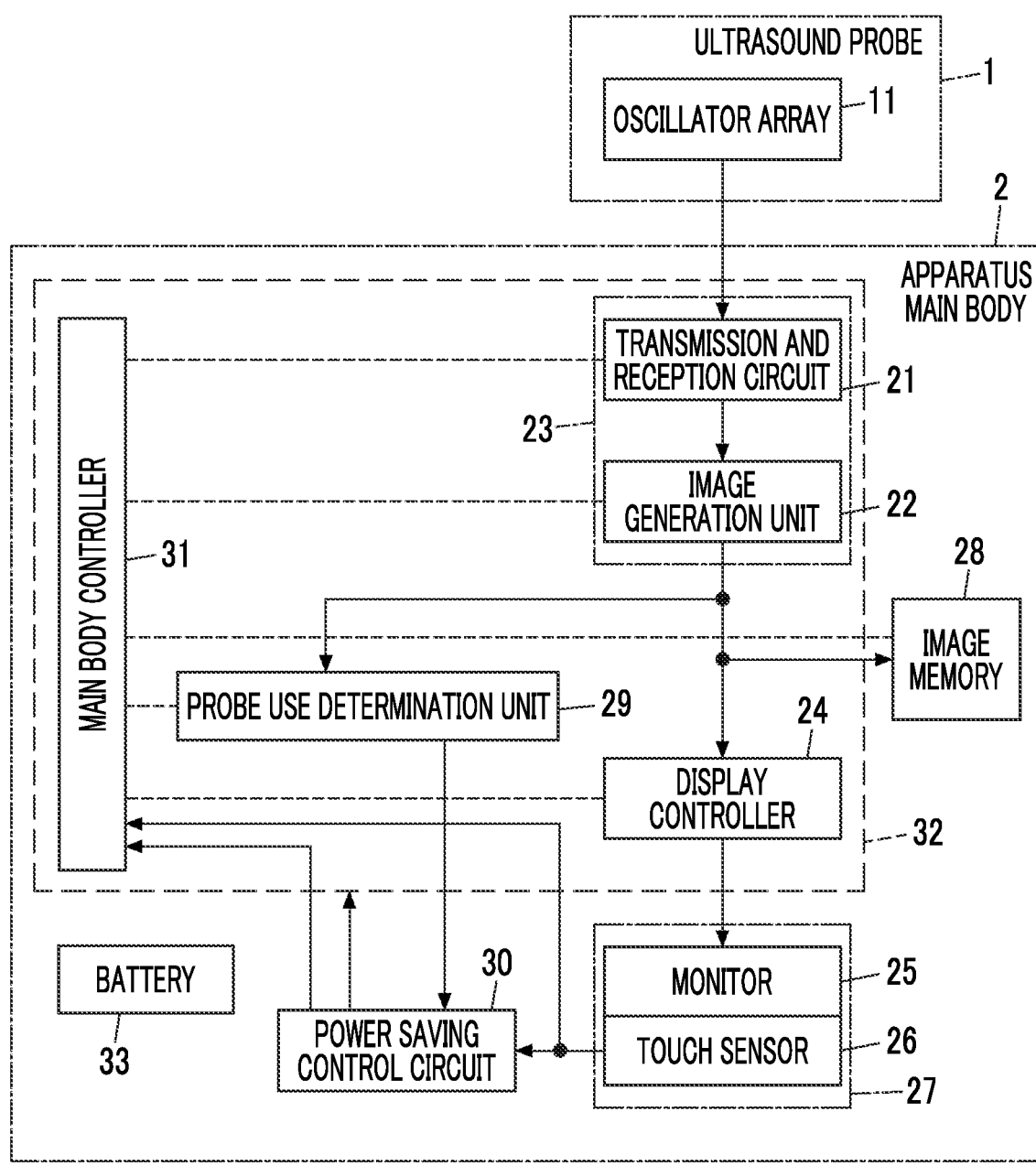
FIG. 1 is a block diagram showing a configuration of an ultrasound diagnostic apparatus according to an embodiment 1 of the present invention.

FIG. 1 shows a configuration of an ultrasound diagnostic apparatus according to an embodiment 1 of the present invention. The ultrasound diagnostic apparatus is an ultrasound diagnostic apparatus that has an ultrasound probe 1 and an apparatus main body 2 connected to the ultrasound probe 1, in which the ultrasound probe 1 and the apparatus main body 2 are connected to each other by wire.

The ultrasound probe 1 has an oscillator array 11.

The apparatus main body 2 has a transmission and reception circuit 21 and an image generation unit 22 that are sequentially connected to the oscillator array 11 of the ultrasound probe 1, and the transmission and reception circuit 21 and the image generation unit 22 form an imaging unit 23.

A display controller 24 and a monitor 25 are sequentially connected to the image generation unit 22, and a touch sensor 26 is disposed so as to overlap the monitor 25. The monitor 25 and the touch sensor 26 form an operation panel 27. Further, an image memory 28 and a probe use determination unit 29 are connected to the image generation unit 22, and a power saving control circuit 30 is connected to the touch sensor 26 and the probe use determination unit 29. A main body controller 31 is connected to the transmission and reception circuit 21, the image generation unit 22, the display controller 24, the touch sensor 26, the image memory 28, and the probe use determination unit 29.

A main body side processor 32 is composed of the transmission and reception circuit 21, the image generation unit 22, the display controller 24, the probe use determination unit 29, and the main body controller 31.

The power saving control circuit 30 is connected to the main body controller 31 and the main body side processor 32.

In addition, the apparatus main body 2 has a battery 33.

The oscillator array 11 of the ultrasound probe 1 has a plurality of ultrasound oscillators arranged one-dimensionally or two-dimensionally. Each of these oscillators transmits an ultrasound wave in accordance with a drive signal supplied from the transmission and reception circuit 21 of the apparatus main body 2 and outputs an analog reception signal by receiving a reflected wave from a subject. For example, each oscillator is configured by forming electrodes at both ends of a piezoelectric body containing piezoelectric ceramic represented by Lead Zirconate Titanate (PZT), a polymer piezoelectric element represented by Poly Vinylidene Di Fluoride (PVDF), piezoelectric single crystal represented by Lead Magnesium Niobate-Lead Titanate (PMN-PT), or the like.

Figure 2:
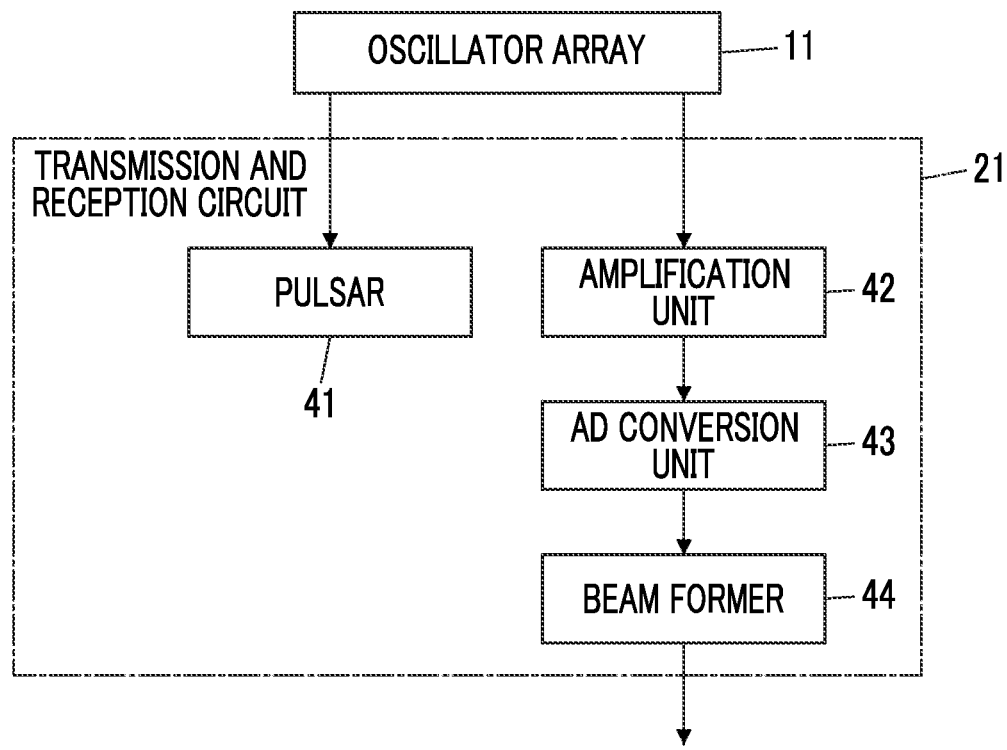
FIG. 2 is a block diagram showing an internal configuration of a transmission and reception circuit in the embodiment 1.

Under the control of the main body controller 31, the transmission and reception circuit 21 of the apparatus main body 2 transmits ultrasound waves from the oscillator array 11 and generates a sound ray signal on the basis of the reception signal acquired by the oscillator array 11. As shown in FIG. 2, the transmission and reception circuit 21 has a pulsar 41 connected to the oscillator array 11, an amplification unit 42, an Analog Digital (AD) conversion unit 43, and a beam former 44 that are sequentially connected in series to the oscillator array 11.

The pulsar 41 includes, for example, a plurality of pulse generators, and supplies respective drive signals to the plurality of oscillators by adjusting amounts of delay such that ultrasound waves transmitted from the plurality of oscillators of the oscillator array 11 form an ultrasound beam, on the basis of a transmission delay pattern selected according to a control signal from the main body controller 31. In this manner, in a case in which a pulsed or continuous-wave voltage is applied to the electrodes of the oscillator of the oscillator array 11, the piezoelectric body expands and contracts to generate a pulsed or continuous-wave ultrasound wave from each of the oscillators, whereby the ultrasound beam is formed from a combined wave of these ultrasound waves.

The transmitted ultrasound beam is reflected by a target, for example, a site of the subject, and an ultrasound echo propagates toward the oscillator array 11 of the ultrasound probe 1. The ultrasound echo propagating toward the oscillator array 11 in this manner is received by each of the oscillators constituting the oscillator array 11. At this time, each of the oscillators constituting the oscillator array 11 expands and contracts by receiving the propagating ultrasound echo, generates a reception signal, which is an electrical signal, and outputs the reception signal to the amplification unit 42.

The amplification unit 42 amplifies the signal input from each of the oscillators constituting the oscillator array 11 and transmits the amplified signal to the AD conversion unit 43. The AD conversion unit 43 converts the signal transmitted from the amplification unit 42 into digital reception data and transmits the reception data to the beam former 44. The beam former 44 performs so-called reception focus processing by giving and adding delay with respect to each reception data converted by the AD conversion unit 43, in accordance with a sound velocity or a sound velocity distribution set on the basis of a reception delay pattern selected according to a control signal from the main body controller 31. By this reception focus processing, each reception data converted by the AD conversion unit 43 is phase-added, and a sound ray signal in which the focus of the ultrasound echo is narrowed down is acquired.

Figure 3:
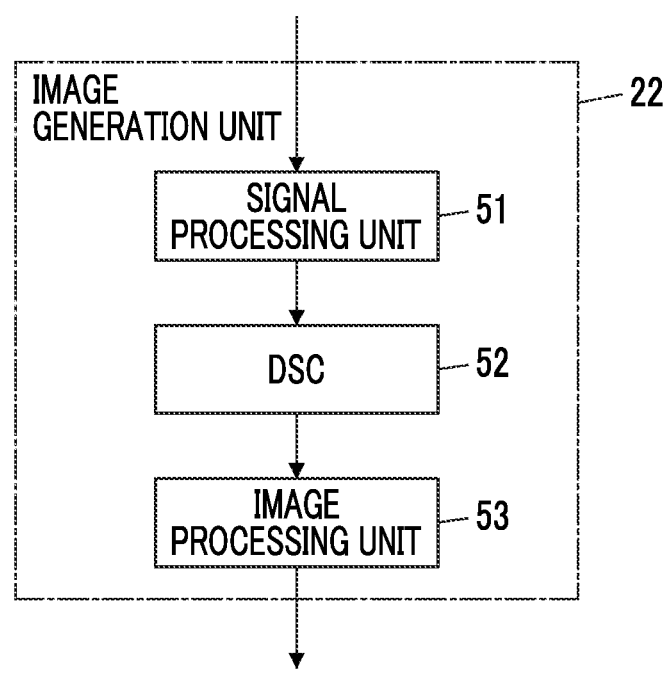
FIG. 3 is a block diagram showing an internal configuration of an image generation unit in the embodiment 1.

As shown in FIG. 3, the image generation unit 22 has a configuration in which a signal processing unit 51, a Digital Scan Converter (DSC) 52, and an image processing unit 53 are sequentially connected in series.

The signal processing unit 51 corrects attenuation caused by a distance according to the depth of a reflection position of the ultrasound wave and then performs, on the sound ray signal sent from the transmission and reception circuit 21, envelope detection processing, thereby generating an ultrasound image signal (B-mode image signal) which is tomographic image information regarding a tissue inside the subject.

The DSC 52 converts the ultrasound image signal generated by the signal processing unit 51 into an image signal conforming to a scanning method of a normal television signal (raster conversion).

The image processing unit 53 performs various types of necessary image processing, such as gradation processing, on the ultrasound image signal input from the DSC 52, and then outputs a signal representing an ultrasound image (hereinafter, referred to as an ultrasound image) to the display controller 24.

The transmission and reception circuit 21 and the image generation unit 22 form the imaging unit 23 that transmits and receives the ultrasound beam to and from the subject through the oscillator array 11 and that generates the ultrasound image on the basis of the reception signal output from the oscillator array 11.

The display controller 24 displays the ultrasound image generated by the image generation unit 22 on the monitor 25 as a display image.

The monitor 25 is controlled by the display controller 24 to display the ultrasound image as the display image, and examples thereof include a display device, such as a Liquid Crystal Display (LCD) and an Organic Electroluminescence Display (organic EL display).

The touch sensor 26 is disposed on a display screen of the monitor 25 so as to overlap each other, and is for performing an input operation through a so-called touch operation in which a user's finger, a stylus pen, or the like is brought into contact with or close to the display screen. The output signal from the touch sensor 26 is sent to the power saving control circuit 30 and the main body controller 31.

The monitor 25 and the touch sensor 26 constitute the operation panel 27 for the user to perform an input operation.

The image memory 28 is a memory that stores the ultrasound image generated by the image generation unit 22 under the control of the main body controller 31. For example, the image memory 28 can hold ultrasound images of a plurality of frames generated by the image generation unit 22 in response to the diagnosis for the subject.

As the image memory 28, recording media, such as a flash memory, a Hard Disc Drive (HDD), a Solid State Drive (SSD), a Flexible Disc (FD), a Magneto-Optical disc (MO disc), a Magnetic Tape (MT), a Random Access Memory (RAM), a Compact Disc (CD), a Digital Versatile Disc (DVD), a Secure Digital card (SD card), and a Universal Serial Bus memory (USB memory), can be used.

The probe use determination unit 29 analyzes the ultrasound image generated by the image generation unit 22 to determine whether or not the ultrasound probe 1 is being used for ultrasonic examination. Specifically, whether or not the ultrasound probe 1 is being used is determined according to whether the ultrasound image shows a tomographic image of the subject, shows a midair radiation state of the ultrasound probe 1 to which jelly is not applied, or shows the midair radiation state of the ultrasound probe 1 to which jelly is applied.

Figure 4:
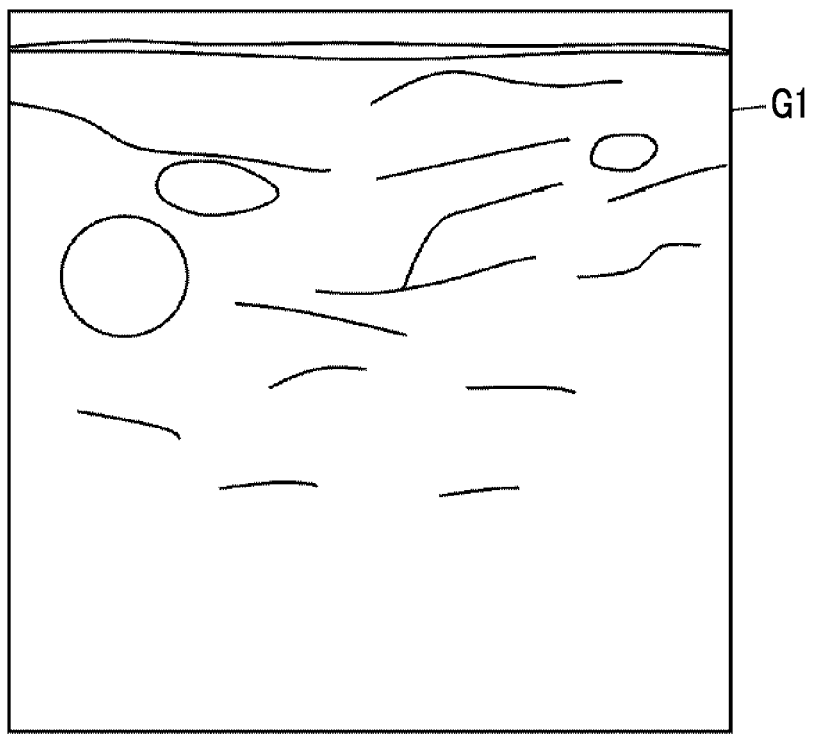
FIG. 4 is a diagram showing an ultrasound image in which an inside of a subject is captured.

For example, as in an ultrasound image G1 shown in FIG. 4, in a case in which a body tissue of the subject is imaged as a structure in an image, inference can be made that the oscillator array 11 of the ultrasound probe 1 to which jelly is applied is in contact with a body surface of the subject.

Figure 5:
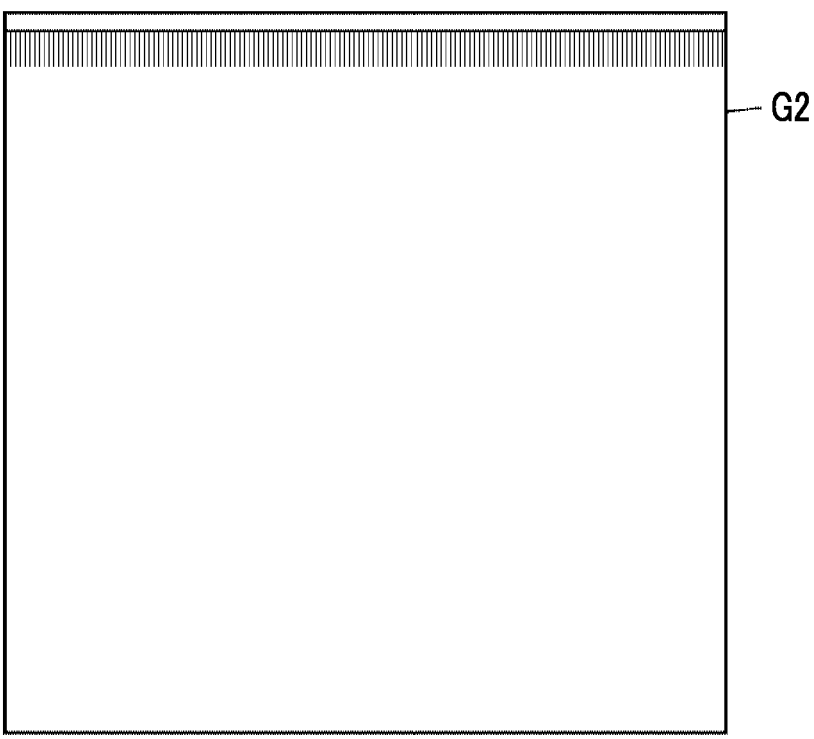
FIG. 5 is a diagram showing an ultrasound image in a case in which an ultrasound probe to which jelly is not applied is in a midair radiation state.

On the other hand, as in an ultrasound image G2 shown in FIG. 5, in a case in which the entire image shows low brightness substantially uniformly and neither the structure nor the wave-front of the ultrasound echo can be confirmed in the image, inference can be made that the ultrasound probe 1 to which jelly is not applied is in the midair radiation state.

Figure 6:
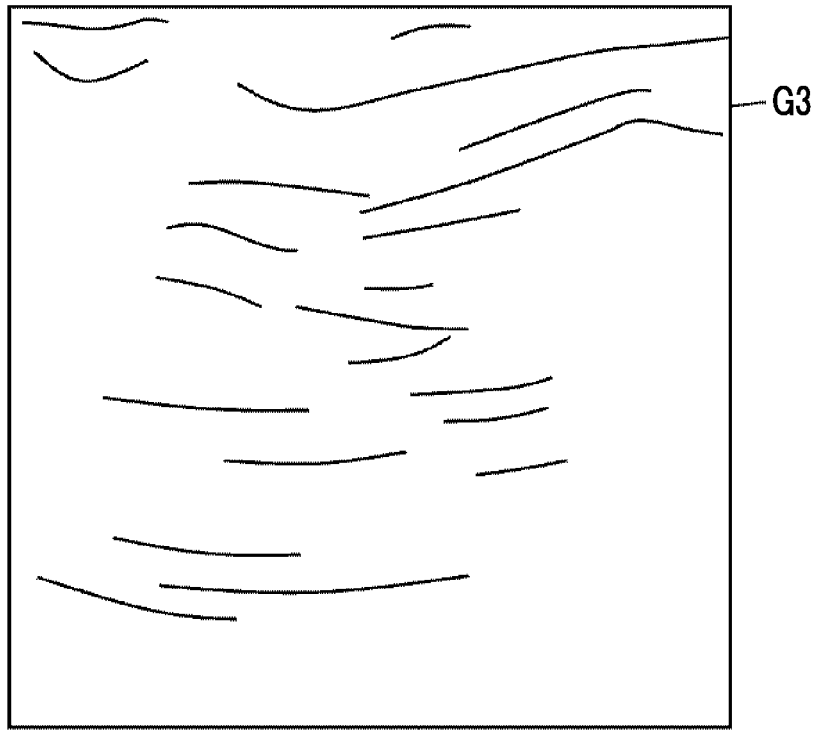
FIG. 6 is a diagram showing an ultrasound image in a case in which the ultrasound probe to which jelly is applied is in the midair radiation state.

Further, as in an ultrasound image G3 shown in FIG. 6, in a case in which the structure is not confirmed in the image but the wave-front of the ultrasound echo can be confirmed, determination can be made that the ultrasound probe 1 to which jelly is applied is in the midair radiation state, and inference can be made that the oscillator array 11 of the ultrasound probe 1 is not in contact with the body surface of the subject but the ultrasound probe 1 is in use or will soon be used.

In that respect, the probe use determination unit 29 determines that the ultrasound probe 1 is being used, in a case in which the ultrasound image shows that jelly is applied to the ultrasound probe 1 or that the ultrasound probe 1 is not in the midair radiation state, as in the ultrasound image G1 shown in FIG. 4 and the ultrasound image G3 shown in FIG. 6. On the other hand, the probe use determination unit 29 determines that the ultrasound probe 1 is not being used, in a case in which the ultrasound image shows that jelly is not applied to the ultrasound probe 1 and that the ultrasound probe 1 is in the midair radiation state, as in the ultrasound image G2 shown in FIG. 5.

Such an ultrasound image analysis can be performed by using at least one of a template matching, an image analysis technology using a feature amount, such as Adaptive Boosting (Adaboost), Support Vector Machine (SVM), or Scale-Invariant Feature Transform (SIFT), or a determination model trained using a machine learning technology, such as deep learning. The determination model is a trained model that has learned a jelly-applied state, an unapplied state, and a midair radiation state.

The power saving control circuit 30 controls the operations of the ultrasound probe 1 and the apparatus main body 2 by selecting one operation mode from among a normal mode and a power saving mode on the basis of a determination result of the probe use determination unit 29 as to whether or not the ultrasound probe 1 is being used and the presence or absence of the operation of the operation panel 27 detected by the touch sensor 26.

Specifically, in the normal mode in which the ultrasound probe 1 and the apparatus main body 2 are normally operated, in a case in which a state in which the probe use determination unit 29 determines that the ultrasound probe 1 is not being used and the touch sensor 26 detects that the operation panel 27 is not being operated continues for a predetermined time T0, the power saving control circuit 30 selects the power saving mode to switch the normal mode to the power saving mode.

The time T0 can be set to, for example, 5 to 10 minutes.

The power saving mode is an operation mode in which power consumption of at least a part of the ultrasound probe 1 and the apparatus main body 2 is reduced. In the power saving mode, the power saving control circuit 30 can control, for example, the main body controller 31 or the main body side processor 32 to perform processing of:
(1) reducing the power consumption in the imaging unit 23 while transmitting and receiving ultrasound waves through the oscillator array 11;
(2) stopping the operation of the imaging unit 23;
(3) stopping the operation of the main body side processor 32; and the like.

The main body controller 31 controls each unit of the apparatus main body 2 on the basis of a program stored in advance in a storage unit (not shown) or the like and an input operation of the user performed via the operation panel 27.

The battery 33 supplies power to each of the imaging unit 23, the display controller 24, the operation panel 27, the probe use determination unit 29, the power saving control circuit 30, and the main body controller 31, which are provided in the apparatus main body 2.

Although the main body side processor 32 having the transmission and reception circuit 21, the image generation unit 22, the display controller 24, the probe use determination unit 29, and the main body controller 31 of the apparatus main body 2 may be composed of a Central Processing Unit (CPU) that executes various programs and a control program for causing the CPU to perform various types of processing, the main body side processor 32 may be composed of a Field Programmable Gate Array (FPGA), a Digital Signal Processor (DSP), an Application Specific Integrated Circuit (ASIC), a Graphics Processing Unit (GPU), or other Integrated Circuits (ICs), or may be composed of a combination thereof.

In addition, the transmission and reception circuit 21, the image generation unit 22, the display controller 24, the probe use determination unit 29, and the main body controller 31 of the main body side processor 32 can also be configured by being partially or wholly integrated into one CPU or the like.

Figure 7:
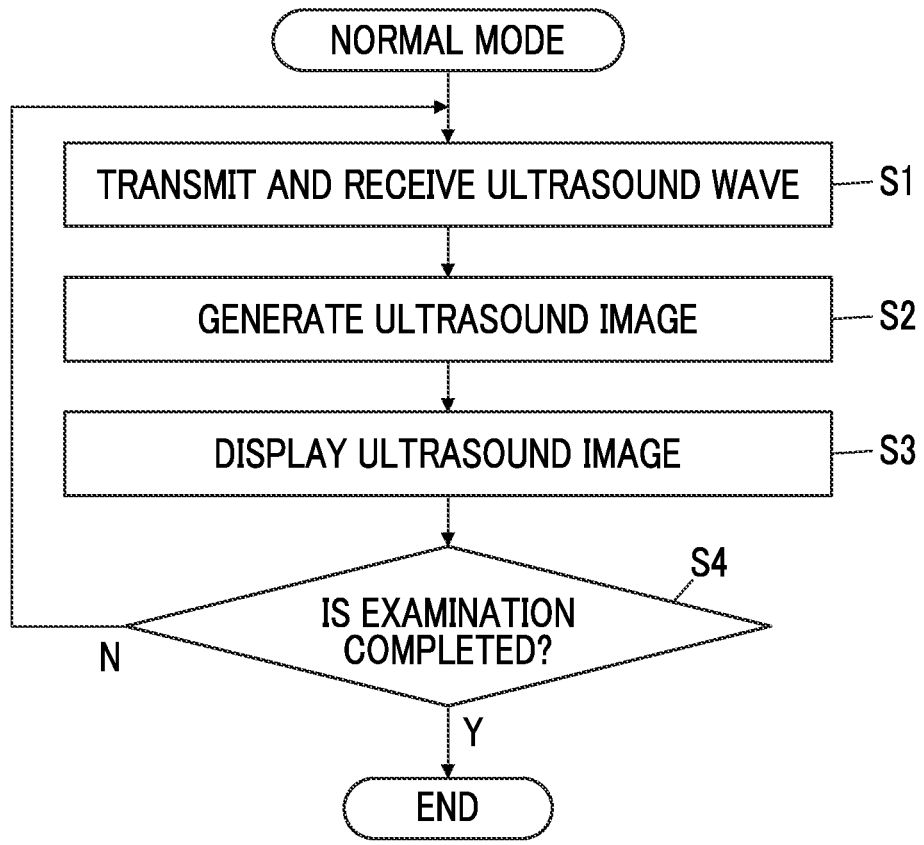
FIG. 7 is a flowchart showing an operation of the ultrasound diagnostic apparatus according to the embodiment 1 in a normal mode.

Next, an operation of the ultrasound diagnostic apparatus according to the embodiment 1 in the normal mode will be described with reference to the flowchart of FIG. 7.

In the normal mode, an output signal from the touch sensor 26 is sent to the main body controller 31 on the basis of the operation of the operation panel 27 performed by the user, and the main body controller 31 controls the operation of each unit provided in the apparatus main body 2.

In a case in which the user gives an instruction for the ultrasonic examination via the operation panel 27, the oscillator array 11 of the ultrasound probe 1 transmits and receives ultrasound waves to and from the subject in step S1.

At this time, under the control of the main body controller 31, ultrasound waves are transmitted from the plurality of oscillators of the oscillator array 11 in accordance with the drive signals from the pulsar 41 of the transmission and reception circuit 21 of the imaging unit 23. The ultrasound echoes reflected by the body tissue of the subject are received by the plurality of oscillators of the oscillator array 11, the reception signals are amplified by being output to the amplification unit 42 and are subjected to AD conversion by the AD conversion unit 43, and then the reception focus processing is performed by the beam former 44, whereby the sound ray signal is generated.

In the subsequent step S2, the ultrasound image is generated by the image generation unit 22 of the imaging unit 23.

The sound ray signal generated by the beam former 44 of the transmission and reception circuit 21 is sent to the image generation unit 22, the attenuation correction corresponding to the depth of the reflection position of the ultrasound wave and the envelope detection processing are performed on the sound ray signal by the signal processing unit 51, the processed signal is converted into the image signal conforming to the scanning method of the normal television signal by the DSC 52, and various types of necessary image processing, such as gradation processing, is performed by the image processing unit 53. In this manner, the ultrasound image is generated by the image generation unit 22.

In step S3, the ultrasound image generated in this manner is sent from the image generation unit 22 to the display controller 24 and is displayed on the monitor 25 via the display controller 24.

At this time, the ultrasound image is also sent from the image generation unit 22 to the image memory 28 and is stored in the image memory 28. Further, the ultrasound image is also sent from the image generation unit 22 to the probe use determination unit 29.

After that, in step S4, whether or not the ultrasonic examination for the subject is completed is determined, and the process returns to step S1 to repeatedly perform steps S1 to S4 in a case in which determination is made that the examination has not yet been completed, and a series of processing ends in a case in which determination is made that the examination is completed.

Next, a shift operation of the ultrasound diagnostic apparatus according to the embodiment 1 from the normal mode to the power saving mode will be described with reference to the flowchart of FIG. 8.

The output signal from the touch sensor 26 of the operation panel 27 and the output signal from the probe use determination unit 29 are input to the power saving control circuit 30 during the operation in the normal mode, and whether or not to shift to the power saving mode is determined by the power saving control circuit 30.

First, in step S11, the determination result of the probe use determination unit 29 as to whether or not the ultrasound probe 1 is being used for the examination of the subject is confirmed. Here, the probe use determination unit 29 analyzes the ultrasound image generated in the normal mode to infer whether the ultrasound image shows a tomographic image of the subject, shows the midair radiation state of the ultrasound probe 1 to which jelly is not applied, or shows the midair radiation state of the ultrasound probe 1 to which jelly is applied.

For example, as in the ultrasound image G1 shown in FIG. 4, in a case in which a body tissue of the subject is imaged as a structure in an image, inference is made that the oscillator array 11 of the ultrasound probe 1 to which jelly is applied is in contact with the body surface of the subject.

On the other hand, as in the ultrasound image G2 shown in FIG. 5, in a case in which the entire image shows low brightness substantially uniformly and neither the structure nor the wave-front of the ultrasound echo can be confirmed in the image, inference is made that the ultrasound probe 1 to which jelly is not applied is in the midair radiation state.

Further, as in the ultrasound image G3 shown in FIG. 6, in a case in which the structure is not confirmed in the image but the wave-front of the ultrasound echo can be confirmed, determination is made that the ultrasound probe 1 to which jelly is applied is in the midair radiation state, and inference is made that the oscillator array 11 of the ultrasound probe 1 is not in contact with the body surface of the subject but the ultrasound probe 1 is in use or will soon be used.

In that respect, the probe use determination unit 29 can determine that the ultrasound probe 1 is being used, in a case in which the ultrasound image shows that jelly is applied to the ultrasound probe 1 or that the ultrasound probe 1 is not in the midair radiation state, as in the ultrasound image G1 shown in FIG. 4 and the ultrasound image G3 shown in FIG. 6, and can determine that the ultrasound probe 1 is not being used, in a case in which the ultrasound image shows that jelly is not applied to the ultrasound probe 1 and that the ultrasound probe 1 is in the midair radiation state, as in the ultrasound image G2 shown in FIG. 5.

In step S11, in a case in which the determination result indicating that the ultrasound probe 1 is being used is sent from the probe use determination unit 29 to the power saving control circuit 30, step S11 is repeatedly performed without shifting to the power saving mode.

On the other hand, in step S11, in a case in which the determination result indicating that the ultrasound probe 1 is not being used is sent from the probe use determination unit 29 to the power saving control circuit 30, the process proceeds to step S12, and whether or not the operation of the operation panel 27 performed by the user is detected is confirmed on the basis of the output signal from the touch sensor 26.

In step S12, in a case in which the operation of the operation panel 27 is detected, determination is made that the examination for the subject, such as viewing the ultrasound image displayed on the monitor 25 and inputting findings regarding the subject, is being performed although the ultrasound probe 1 is not being used, and the process returns to step S11 to repeatedly perform steps S11 and S12 without shifting to the power saving mode.

On the other hand, in step S12, in a case in which the operation of the operation panel 27 is not detected, the process further proceeds to step S13, and whether or not the predetermined time T0 is passed is confirmed.

The process returns to step S11 to repeatedly perform steps S11 to S13 until the passage of the time T0 is confirmed in step S13.

In a case in which determination is made in step S11 that the ultrasound probe 1 is being used or in a case in which the operation of the operation panel 27 is detected in step S12 before the time T0 is passed, determination is made that the examination for the subject is being performed, and the process returns to step S11 without shifting to the power saving mode.

On the other hand, in a case in which determination is made in step S11 that the ultrasound probe 1 is not being used and the passage of the time T0 is confirmed in step S13 while a state in which the operation of the operation panel 27 is not detected in step S12 is maintained, determination is made that the examination for the subject is not being performed from the fact that the ultrasound probe 1 is not being used and the operation panel 27 is also not being operated, and the power saving control circuit 30 shifts the normal mode so far to the power saving mode.

In a case of shifting to the power saving mode in this manner, for example, a power saving instruction is sent from the power saving control circuit 30 to the main body controller 31, and power consumption in the imaging unit 23 is reduced while transmitting and receiving ultrasound waves through the oscillator array 11, under the control of the main body controller 31. Specifically, it is possible to generate the ultrasound image by reducing a frame rate of the transmission and reception of ultrasound waves in the imaging unit 23. That is, the ultrasound image is generated by performing the transmission and reception of ultrasound waves using the oscillator array 11 of the ultrasound probe 1 at a frame rate lower than a frame rate in the normal mode. Therefore, the power consumption in the imaging unit 23 is reduced.

In addition, it is also possible to reduce the power consumption in the imaging unit 23, for example, by reducing the drive voltage supplied from the pulsar 41 of the transmission and reception circuit 21 to the plurality of oscillators of the oscillator array 11 to generate the ultrasound image, or by driving only a part of the plurality of oscillators of the oscillator array 11 to generate the ultrasound image.

In addition, the operation of the imaging unit 23 can also be stopped in the power saving mode. With this, the transmission and reception of ultrasound waves using the ultrasound probe 1 and the generation of the ultrasound image are prohibited, and the power consumption in the imaging unit 23 is reduced.

Further, the apparatus main body 2 can also be put into a so-called sleep state by sending an instruction from the power saving control circuit 30 to the main body side processor 32 to stop the entire operation of the main body side processor 32.

Next, a shift operation of the ultrasound diagnostic apparatus according to the embodiment 1 from the power saving mode to the normal mode will be described with reference to the flowchart of FIG. 9.

In the power saving mode, as described above, the power consumption of at least a part of the ultrasound probe 1 and the apparatus main body 2 is reduced, but the power supply from the battery 33 to the operation panel 27 and the power saving control circuit 30 continues.

In that respect, in step S21, whether or not the operation of the operation panel 27 performed by the user is detected is confirmed on the basis of the output signal from the touch sensor 26.

In a case in which the operation of the operation panel 27 is not detected in step S21, step S21 is repeatedly performed without being shifted to the normal mode by the power saving control circuit 30.

On the other hand, in step S21, in a case in which the operation of the operation panel 27 is detected, determination is made that the examination for the subject is started or restarted, and the power saving control circuit 30 shifts the power saving mode to the normal mode.

As described above, according to the embodiment 1, since the power saving control circuit 30 controls the operations of the ultrasound probe 1 and the apparatus main body 2 by selecting one of the normal mode or the power saving mode on the basis of the presence or absence of the operation of the operation panel 27 detected by the touch sensor 26 and the determination result of the probe use determination unit 29 as to whether or not the ultrasound probe 1 is being used, it is possible to reduce the power consumption by reliably detecting the operation status without being bothered by unintended vibration, contact, or the like.

In the above-described embodiment 1, the imaging unit 23 consisting of the transmission and reception circuit 21 and the image generation unit 22 is disposed in the apparatus main body 2, but at least a part of the imaging unit 23 can also be disposed in the ultrasound probe 1.

Modification Example of Embodiment 1

In the above-described embodiment 1, although the operation mode shifts from the normal mode to the power saving mode in a case in which a state in which the ultrasound probe 1 is not being used and the operation panel 27 is not being operated continues for the time T0, a configuration can also be employed in which two types of modes, that is, a first mode and a second mode, are set as the power saving mode and the operation mode shifts to the power saving mode in a stepwise manner.

For example, as the first mode, a mode in which only the power consumption in the imaging unit 23 is reduced by stopping the operation of the imaging unit 23, in the ultrasound probe 1 and the apparatus main body 2, can be set, and as the second mode, a mode in which the overall power consumption of the ultrasound probe 1 and the apparatus main body 2 is reduced by stopping the operation of the main body side processor 32 can be set.

Figure 10:
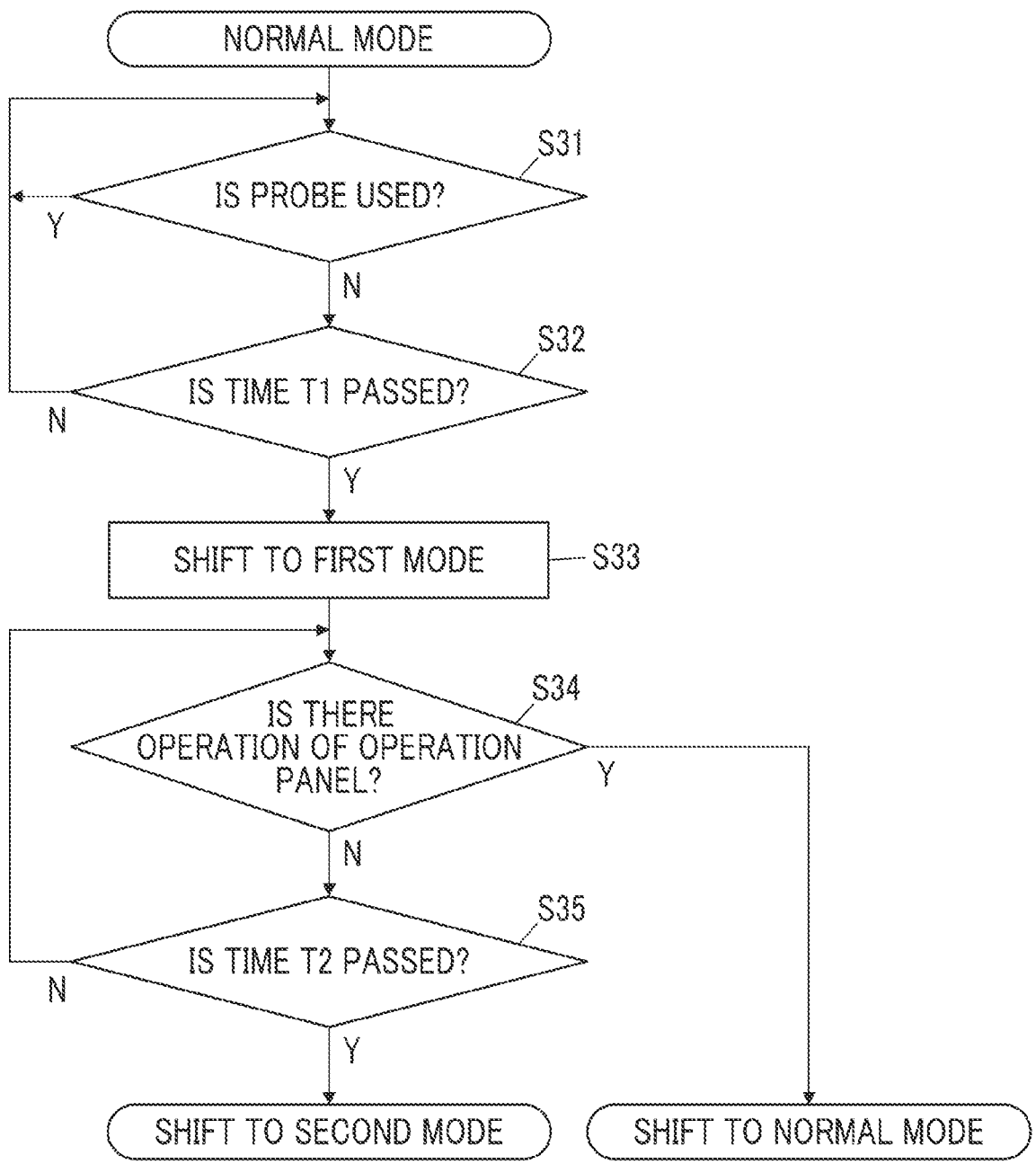
FIG. 10 is a flowchart showing an operation of an ultrasound diagnostic apparatus according to a modification example of the embodiment 1 in a case of shifting from the normal mode to the power saving mode.

Next, a shift operation of an ultrasound diagnostic apparatus according to a modification example of the embodiment 1 from the normal mode to the power saving mode will be described with reference to the flowchart of FIG. 10.

First, in step S31, the determination result of the probe use determination unit 29 as to whether the ultrasound probe 1 is being used for the examination of the subject is confirmed.

In step S31, in a case in which the determination result indicating that the ultrasound probe 1 is being used is sent from the probe use determination unit 29 to the power saving control circuit 30, step S31 is repeatedly performed without shifting to the power saving mode.

On the other hand, in step S31, in a case in which the determination result indicating that the ultrasound probe 1 is not being used is sent from the probe use determination unit 29 to the power saving control circuit 30, the process proceeds to step S32, and whether or not a predetermined time T1 is passed is confirmed.

The process returns to step S31 to repeatedly perform steps S31 and S32 until the passage of the time T1 is confirmed in step S32.

In a case in which determination is made in step S31 that the ultrasound probe 1 is being used before the time T1 is passed, determination is made that the examination for the subject is being performed, and the process returns to step S31 without shifting to the power saving mode.

On the other hand, in a case in which the passage of the time T1 is confirmed in step S32 while a state in which determination is made in step S31 that the ultrasound probe 1 is not being used is maintained, determination is made that ultrasonic imaging using the ultrasound probe 1 is not being performed, the process proceeds to step S33, and the power saving control circuit 30 shifts the normal mode to the first mode.

In the first mode, the operation of the imaging unit 23 is stopped by the main body controller 31. With this, the transmission and reception of ultrasound waves using the ultrasound probe 1 and the generation of the ultrasound image are prohibited, and the power consumption in the imaging unit 23 is reduced.

Further, in step S34, whether or not the operation of the operation panel 27 is detected is confirmed on the basis of the output signal from the touch sensor 26, during the operation in the first mode.

In step S34, in a case in which the operation of the operation panel 27 is detected, determination is made that the examination for the subject is started or restarted, and the power saving control circuit 30 shifts the first mode to the normal mode.

On the other hand, in step S34, in a case in which the operation of the operation panel 27 is not detected, the process proceeds to step S35, and whether or not the predetermined time T2 is passed is confirmed.

The process returns to step S34 to repeatedly perform steps S34 and S35 until the passage of the time T2 is confirmed in step S35.

In a case in which the operation of the operation panel 27 is detected in step S34 before the time T2 is passed, the first mode shifts to the normal mode.

On the other hand, in a case in which the passage of the time T2 is confirmed in step S35 while a state in which the operation of the operation panel 27 is not detected in step S34 is maintained, determination is made that neither the ultrasonic imaging using the ultrasound probe 1, the viewing of the ultrasound image displayed on the monitor 25, nor the input of findings regarding the subject is being performed, and the power saving control circuit 30 shifts the first mode to the second mode.

The times T1 and T2 can each be set to, for example, 5 to 10 minutes.

In the second mode, the apparatus main body 2 is put into a so-called sleep state by sending an instruction from the power saving control circuit 30 to the main body side processor 32 to stop the entire operation of the main body side processor 32. With this, the overall power consumption of the ultrasound probe 1 and the apparatus main body 2 is significantly reduced.

In a case in which the CPU constituting the main body side processor 32 has multistage deep sleep modes, the main body side processor 32 can also be sequentially transitioned to deeper sleep modes as the passage of the time in step S35 increases while a state in which the operation of the operation panel 27 is not detected is maintained.

Embodiment 2

In the above-described embodiment 1, the ultrasound probe 1 and the apparatus main body 2 are connected to each other by wire, but these can also be wirelessly connected.

Figure 11:
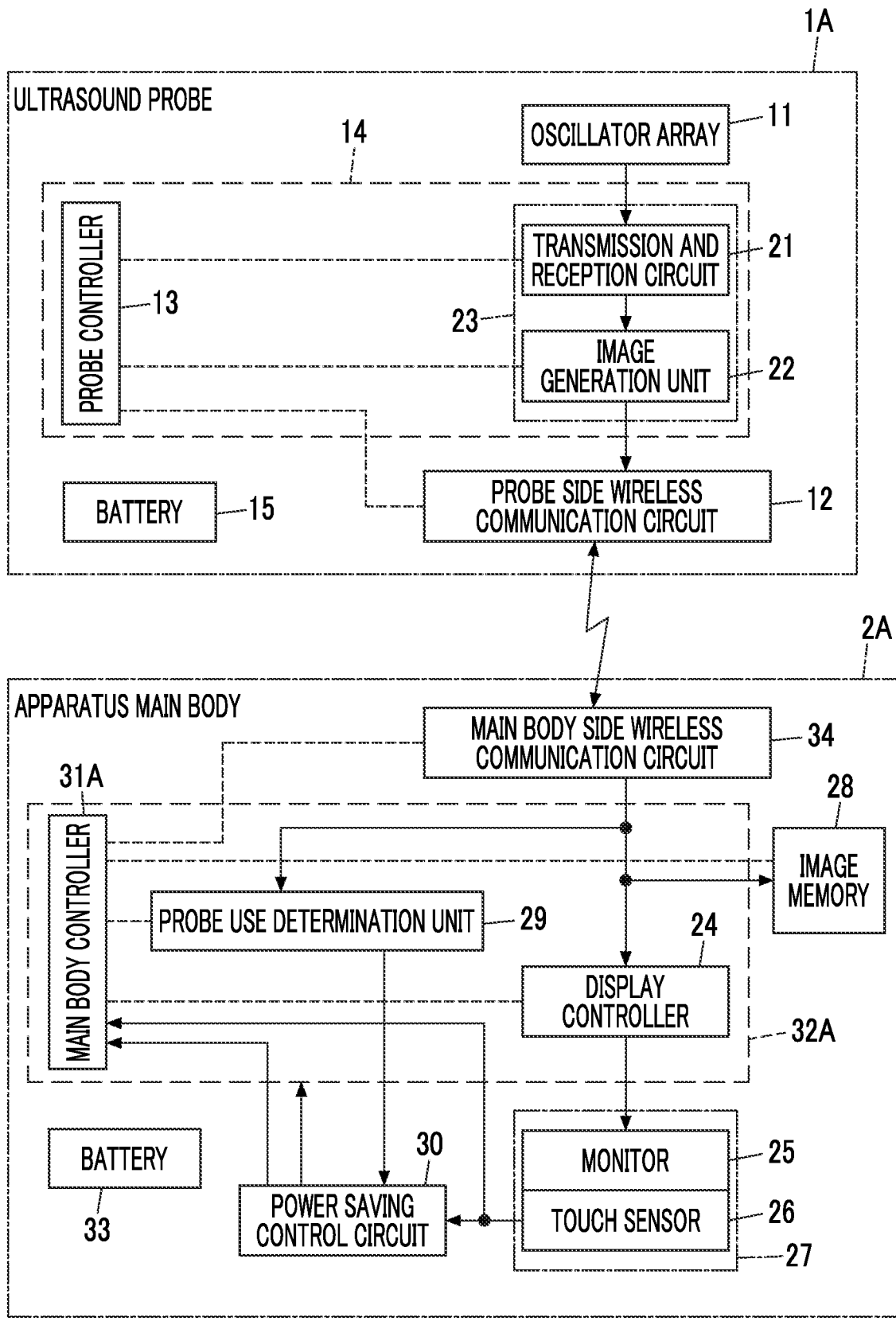
FIG. 11 is a block diagram showing a configuration of an ultrasound diagnostic apparatus according to an embodiment 2.

FIG. 11 shows an ultrasound diagnostic apparatus according to an embodiment 2. The ultrasound diagnostic apparatus of the embodiment 2 has an ultrasound probe 1A and an apparatus main body 2A wirelessly connected to the ultrasound probe 1A.

The ultrasound probe 1A is an ultrasound probe in which the transmission and reception circuit 21, the image generation unit 22, a probe side wireless communication circuit 12, a probe controller 13, and a battery 15 are added to the ultrasound probe 1 in the embodiment 1.

The transmission and reception circuit 21 and the image generation unit 22 are sequentially connected to the oscillator array 11, and the probe side wireless communication circuit 12 is further connected to the image generation unit 22. The probe controller 13 is connected to the transmission and reception circuit 21, the image generation unit 22, and the probe side wireless communication circuit 12.

A probe side processor 14 is composed of the transmission and reception circuit 21, the image generation unit 22, and the probe controller 13.

The apparatus main body 2A is an apparatus main body in which a main body side wireless communication circuit 34 is disposed instead of the imaging unit 23 and a main body controller 31A is disposed instead of the main body controller 31 in the apparatus main body 2 in the embodiment 1. The display controller 24, the image memory 28, and the probe use determination unit 29 are connected to the main body side wireless communication circuit 34.

The main body controller 31A is connected to the display controller 24, the touch sensor 26, the image memory 28, the probe use determination unit 29, the power saving control circuit 30, and the main body side wireless communication circuit 34.

In addition, a main body side processor 32A is composed of the display controller 24, the probe use determination unit 29, and the main body controller 31A.

The transmission and reception circuit 21 and the image generation unit 22 of the ultrasound probe 1A are the same as the transmission and reception circuit 21 and the image generation unit 22 disposed in the apparatus main body 2 in the embodiment 1, and form the imaging unit 23.

The probe side wireless communication circuit 12 performs wireless communication with the main body side wireless communication circuit 34 of the apparatus main body 2A, includes an antenna for transmitting and receiving radio waves, generates a transmission signal by modulating a carrier on the basis of the ultrasound image generated by the image generation unit 22, and transmits the radio waves from the antenna by supplying the transmission signal to the antenna, thereby wirelessly transmitting the ultrasound image to the main body side wireless communication circuit 34 of the apparatus main body 2A. As a carrier modulation method, Amplitude Shift Keying (ASK), Phase Shift Keying (PSK), Quadrature Phase Shift Keying (QPSK), and 16 Quadrature Amplitude Modulation (16QAM) and the like are used.

Further, the probe side wireless communication circuit 12 transmits various signals sent from the probe controller 13 to the main body side wireless communication circuit 34 of the apparatus main body 2A, and receives various signals transmitted from the main body side wireless communication circuit 34 of the apparatus main body 2A to send the various signals to the probe controller 13.

The probe controller 13 controls the transmission and reception circuit 21 and the image generation unit 22 on the basis of a program or the like stored in advance.

In addition, the battery 15 supplies power to each of the transmission and reception circuit 21, the image generation unit 22, the probe side wireless communication circuit 12, and the probe controller 13, which are provided in the ultrasound probe 1A.

The probe side processor 14 having the transmission and reception circuit 21, the image generation unit 22, and the probe controller 13 of the ultrasound probe 1A is composed of a CPU that executes various programs and a control program for causing the CPU to perform various types of processing, but the probe side processor 14 may be composed of FPGA, DSP, ASIC, GPU, or other ICs, or may be composed of a combination thereof.

In addition, the transmission and reception circuit 21, the image generation unit 22, and the probe controller 13 of the probe side processor 14 can also be configured by being partially or wholly integrated into one CPU or the like.

The main body side wireless communication circuit 34 of the apparatus main body 2A corresponds to the probe side wireless communication circuit 12 of the ultrasound probe 1A, includes an antenna for transmitting and receiving radio waves, receives the transmission signal transmitted from the probe side wireless communication circuit 12 of the ultrasound probe 1A via the antenna, and demodulates the received transmission signal, thereby sending the ultrasound image to the display controller 24, the image memory 28, and the probe use determination unit 29.

Further, the main body side wireless communication circuit 34 receives various signals transmitted from the probe side wireless communication circuit 12 of the ultrasound probe 1A to send the various signals to the main body controller 31A, and transmits various signals sent from the main body controller 31A to the probe side wireless communication circuit 12 of the ultrasound probe 1A.

The main body controller 31A controls each unit of the apparatus main body 2A on the basis of a program stored in advance in a storage unit (not shown) or the like and an input operation of the user performed via the operation panel 27.

At the time of capturing the ultrasound image in the normal mode, the transmission and reception circuit 21 transmits and receives ultrasound waves by using the oscillator array 11 under the control of the probe controller 13, and the image generation unit 22 generates the ultrasound image. The ultrasound image is wirelessly transmitted from the probe side wireless communication circuit 12 toward the apparatus main body 2A, and the ultrasound image received by the main body side wireless communication circuit 34 of the apparatus main body 2A is displayed on the monitor 25 via the display controller 24.

The shift operation from the normal mode to the power saving mode in the embodiment 2 is the same as the shift operation in the embodiment 1.

The ultrasound image received by the main body side wireless communication circuit 34 of the apparatus main body 2A is analyzed by the probe use determination unit 29, whether or not the ultrasound probe 1A is being used for the examination of the subject is determined, and then the determination result is sent to the power saving control circuit 30. Further, the output signal from the touch sensor 26 is input to the power saving control circuit 30.

Figure 8:
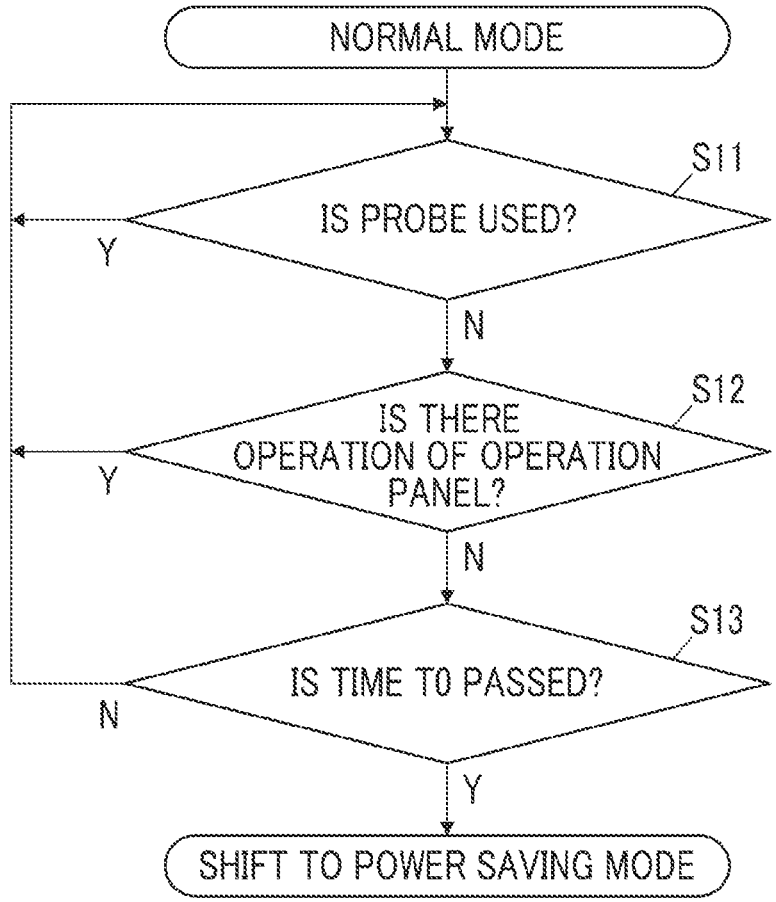
FIG. 8 is a flowchart showing an operation of the ultrasound diagnostic apparatus according to the embodiment 1 in a case of shifting from the normal mode to a power saving mode.

As in the shift operation of the embodiment 1 shown in the flowchart of FIG. 8, in step S11, the power saving control circuit 30 confirms whether or not the ultrasound probe 1 is being used for the examination of the subject on the basis of the determination result of the probe use determination unit 29, and in step S12, further confirms whether or not the operation of the operation panel 27 performed by the user is detected on the basis of the output signal from the touch sensor 26.

In a case in which determination is made that the ultrasound probe 1 is not being used and the passage of the time T0 is confirmed in step S13 while a state in which the operation of the operation panel 27 is not detected is maintained, determination is made that the examination for the subject is not being performed, and the power saving control circuit 30 shifts the normal mode to the power saving mode.

In the embodiment 2, in the power saving mode, for example, a power saving instruction output from the power saving control circuit 30 is transmitted to the ultrasound probe 1A by way of the main body controller 31A and the main body side wireless communication circuit 34, and is further sent to the probe controller 13 by being received by the probe side wireless communication circuit 12.

Then, under the control of the probe controller 13, as in the embodiment 1, for example, the frame rate is reduced, the drive voltage supplied to the plurality of oscillators of the oscillator array 11 is reduced, or only a part of the plurality of oscillators of the oscillator array 11 is driven, whereby the power consumption in the imaging unit 23 can be reduced.

Further, in the embodiment 2, the probe controller 13 may control the probe side wireless communication circuit 12 to perform wireless communication with the main body side wireless communication circuit 34 of the apparatus main body 2A at a communication interval longer than a communication interval in the normal mode. Even in this manner, the power consumption in the ultrasound probe 1A can be reduced.

In addition, the operation of the imaging unit 23 may be stopped in the power saving mode.

Further, the apparatus main body 2A can also be put into a so-called sleep state by sending an instruction from the power saving control circuit 30 to the main body side processor 32A to stop the entire operation of the main body side processor 32A.

The shift operation from the power saving mode to the normal mode in the embodiment 2 is the same as the shift operation in the embodiment 1.

Figure 9:
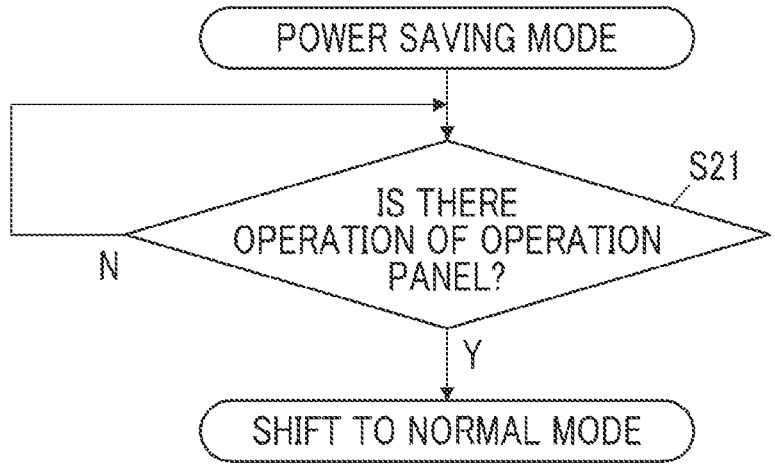
FIG. 9 is a flowchart showing an operation of the ultrasound diagnostic apparatus according to the embodiment 1 in a case of shifting from the power saving mode to the normal mode.

As in the shift operation of the embodiment 1 shown in the flowchart of FIG. 9, in step S21, whether or not the operation of the operation panel 27 performed by the user is detected is confirmed on the basis of the output signal from the touch sensor 26, and the power saving control circuit 30 shifts the power saving mode to the normal mode in a case in which the operation of the operation panel 27 is detected.

Embodiment 3

Figure 12:
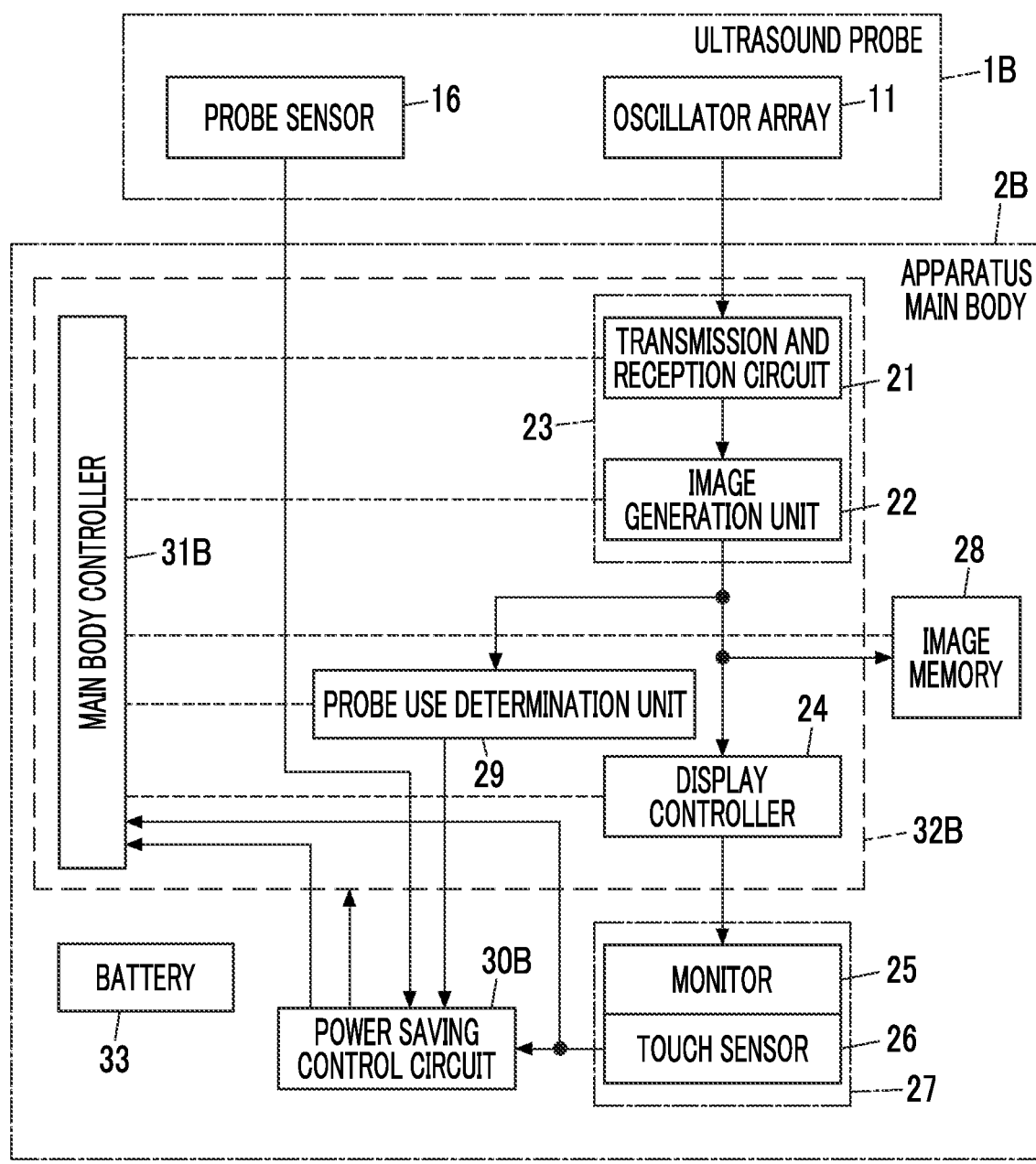
FIG. 12 is a block diagram showing a configuration of an ultrasound diagnostic apparatus according to an embodiment 3.

FIG. 12 shows a configuration of an ultrasound diagnostic apparatus according to an embodiment 3. The ultrasound diagnostic apparatus of the embodiment 3 has an ultrasound probe 1B and an apparatus main body 2B connected to the ultrasound probe 1B by wire.

The ultrasound probe 1B is an ultrasound probe in which a probe sensor 16 is mounted in the ultrasound probe 1 used in the ultrasound diagnostic apparatus of the embodiment 1 shown in FIG. 1.

The apparatus main body 2B is an apparatus main body in which a power saving control circuit 30B and a main body controller 31B are disposed instead of the power saving control circuit 30 and the main body controller 31 in the apparatus main body 2 used in the ultrasound diagnostic apparatus of the embodiment 1, and the other configurations are the same as those of the apparatus main body 2 in the embodiment 1.

The touch sensor 26, the probe use determination unit 29, and the probe sensor 16 of the ultrasound probe 1B are connected to the power saving control circuit 30B.

The transmission and reception circuit 21, the image generation unit 22, the display controller 24, the touch sensor 26, the image memory 28, the probe use determination unit 29, and the power saving control circuit 30B are connected to the main body controller 31B.

In addition, a main body side processor 32B is composed of the transmission and reception circuit 21, the image generation unit 22, the display controller 24, the probe use determination unit 29, and the main body controller 31B.

The probe sensor 16 of the ultrasound probe 1B detects that the ultrasound probe 1B is gripped by the user, and, for example, at least one of a pressure sensor, a capacitance sensor, or a temperature sensor mounted in a grip portion of the ultrasound probe 1B is used as the probe sensor 16.

In a case in which a change in pressure sensed by the pressure sensor, a change in capacitance sensed by the capacitance sensor, or a change in temperature sensed by the temperature sensor exceeds a predetermined threshold value, the probe sensor 16 sends a detection signal indicating that the ultrasound probe 1B is gripped to the power saving control circuit 30B of the apparatus main body 2B.

The power saving control circuit 30B can confirm whether or not the ultrasound probe 1B is gripped on the basis of the detection signal from the probe sensor 16.

The shift operation from the normal mode to the power saving mode in the embodiment 3 is the same as the shift operation in the embodiment 1 shown in the flowchart of FIG. 8.

That is, in a case in which determination is made in step S11 that the ultrasound probe 1 is not being used and the passage of the time T0 is confirmed in step S13 while a state in which the operation of the operation panel 27 is not detected in step S12 is maintained, determination is made that the examination for the subject is not being performed, and the power saving control circuit 30B shifts the normal mode to the power saving mode.

Figure 13:
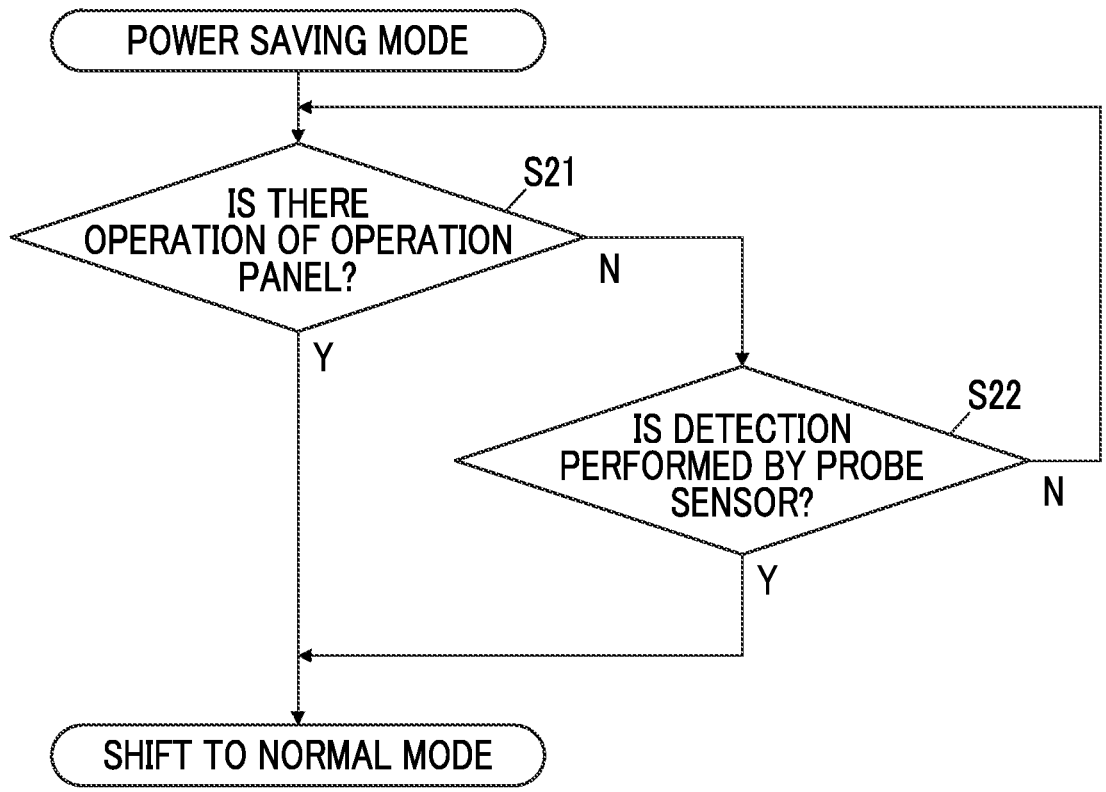
FIG. 13 is a flowchart showing an operation of the ultrasound diagnostic apparatus according to the embodiment 3 in a case of shifting from the power saving mode to the normal mode.

Next, a shift operation of the ultrasound diagnostic apparatus according to the embodiment 3 from the power saving mode to the normal mode will be described with reference to the flowchart of FIG. 13.

In step S21, the power saving control circuit 30B confirms whether or not the operation of the operation panel 27 performed by the user is detected, on the basis of the output signal from the touch sensor 26, the process proceeds to step S22 in a case in which the operation of the operation panel 27 is not detected, and whether or not the ultrasound probe 1B is gripped is confirmed on the basis of the detection signal from the probe sensor 16.

In a case in which the gripping of the ultrasound probe 1B is not detected in step S22, steps S21 and S22 are repeatedly performed without shifting to the normal mode.

On the other hand, in a case in which the operation of the operation panel 27 is detected in step S21 or in a case in which the gripping of the ultrasound probe 1B is detected in step S22, determination is made that the examination for the subject is started or restarted, and the power saving control circuit 30B shifts the power saving mode to the normal mode.

As described above, according to the embodiment 3, not only in a case in which the operation of the operation panel 27 is detected but also in a case in which the gripping of the ultrasound probe 1B is detected, the power saving mode can shift to the normal mode.

Therefore, even in a state in which the generation of the ultrasound image is prohibited because the operation of the imaging unit 23 is stopped or the operation of the main body side processor 32 is stopped in the power saving mode, it is possible to return to the normal mode from the power saving mode by detecting that the ultrasound probe 1B is gripped by the user on the basis of the detection signal from the probe sensor 16 mounted in the ultrasound probe 1B without requiring the analysis of the ultrasound image.

Embodiment 4

In the above-described embodiment 3, the ultrasound probe 1B and the apparatus main body 2B are connected to each other by wire, but these can also be wirelessly connected.

Figure 14:
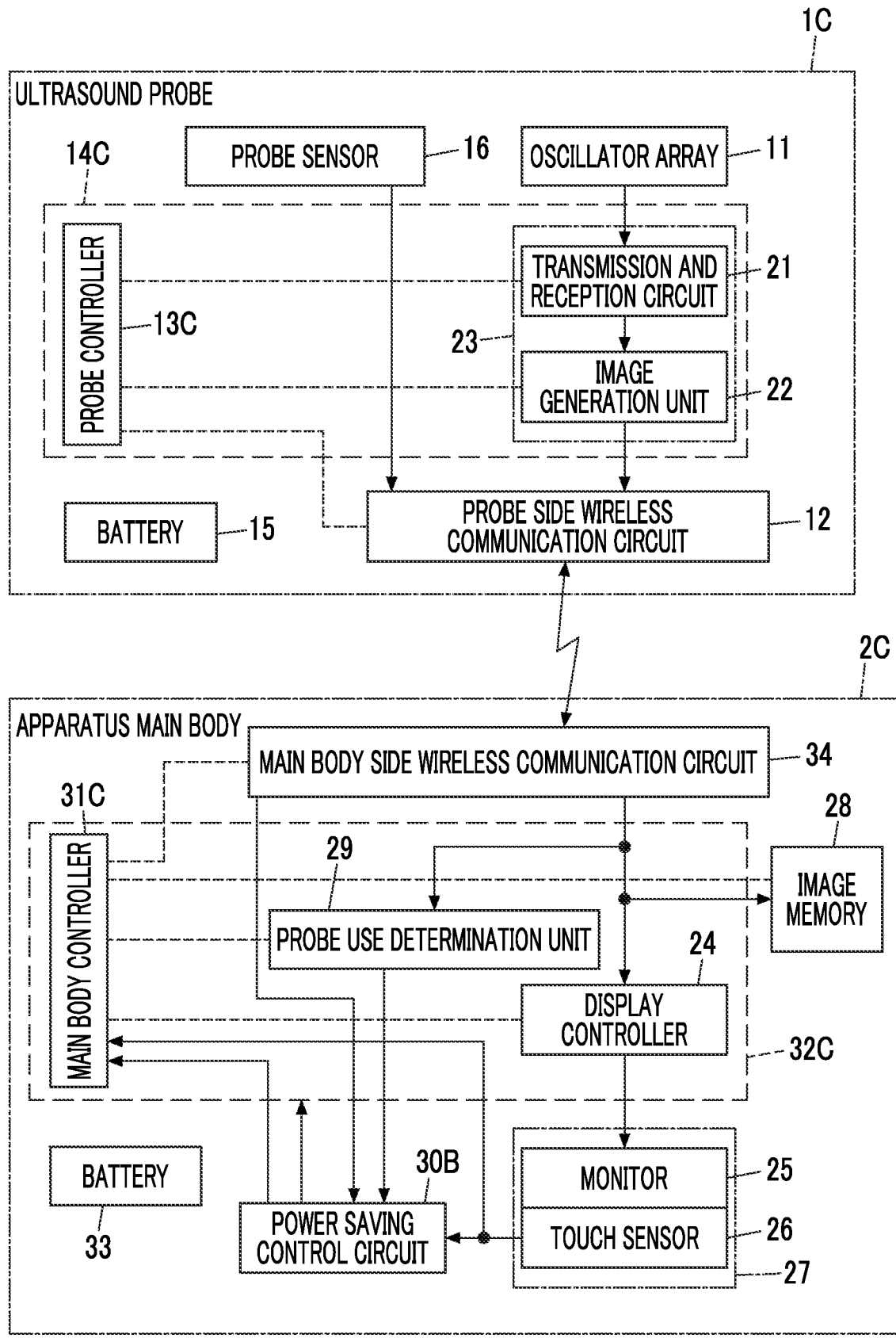
FIG. 14 is a block diagram showing a configuration of an ultrasound diagnostic apparatus according to an embodiment 4.

FIG. 14 shows a configuration of an ultrasound diagnostic apparatus according to an embodiment 4. The ultrasound diagnostic apparatus of the embodiment 4 has an ultrasound probe 1C and an apparatus main body 2C wirelessly connected to the ultrasound probe 1C.

The ultrasound probe 1C is an ultrasound probe in which the probe sensor 16 is mounted and a probe controller 13C is disposed instead of the probe controller 13 in the ultrasound probe 1A used in the ultrasound diagnostic apparatus of the embodiment 2 shown in FIG. 11, and the other configurations are the same as those of the ultrasound probe 1A in the embodiment 2.

The probe controller 13C is connected to the transmission and reception circuit 21, the image generation unit 22, and the probe side wireless communication circuit 12.

A probe side processor 14C is composed of the transmission and reception circuit 21, the image generation unit 22, and the probe controller 13C.

The apparatus main body 2C is an apparatus main body in which a main body controller 31C is disposed instead of the main body controller 31A in the apparatus main body 2A used in the ultrasound diagnostic apparatus of the embodiment 2 shown in FIG. 11, and the other configurations are the same as those of the apparatus main body 2A in the embodiment 2.

The main body controller 31C is connected to the display controller 24, the touch sensor 26, the image memory 28, the probe use determination unit 29, the power saving control circuit 30B, and the main body side wireless communication circuit 34.

In addition, a main body side processor 32C is composed of the display controller 24, the probe use determination unit 29, and the main body controller 31C.

The detection signal output from the probe sensor 16 of the ultrasound probe 1C is wirelessly transmitted from the probe side wireless communication circuit 12 to the apparatus main body 2C under the control of the probe controller 13C, and is sent to the power saving control circuit 30B by being received by the main body side wireless communication circuit 34.

In that respect, as in the embodiment 3, not only in a case in which the operation of the operation panel 27 is detected but also in a case in which the gripping of the ultrasound probe 1C is detected, the power saving control circuit 30B can shift the power saving mode to the normal mode.

Embodiment 5

In the above-described embodiments 1 to 4, the shift between the normal mode and the power saving mode is automatically performed on the basis of the presence or absence of the operation of the operation panel 27 and the determination result of the probe use determination unit 29, but a configuration may be employed in which the user can forcibly perform a manual mode change.

For example, in the power saving mode, in a case in which the touch sensor 26 detects that the operation panel 27 is brought into contact in a predetermined first contact pattern, the power saving control circuits 30 and 30B can switch the power saving mode to the normal mode by determining that the mode change is requested by the user.

As the first contact pattern, for example, various patterns, such as tapping the operation panel 27 twice at high speed, drawing a horizontal bar mark or a checkmark on the operation panel 27, drawing a predetermined figure, such as a circle and a polygon, on the operation panel 27, and drawing a predetermined character or number on the operation panel 27, can be used.

Further, in the normal mode, in a case in which the touch sensor 26 detects that the operation panel 27 is brought into contact in a predetermined second contact pattern, the power saving control circuits 30 and 30B can also switch the normal mode to the power saving mode by determining that the mode change is requested by the user.

As the second contact pattern, the same pattern as the above-described first contact pattern can be used. In this case, the user does not need to store a plurality of contact patterns and can easily switch the mode.

Further, as the second contact pattern, a pattern different from the first contact pattern may be used. In this case, it is possible to switch the mode by clearly grasping the user's intention regarding the shift to the power saving mode and the shift to the normal mode.

As the apparatus main bodies 2, 2A, 2B, and 2C in the above-described embodiments 1 to 5, a portable or handheld compact apparatus main body can also be used, or a stationary apparatus main body can also be used. The apparatus main bodies 2, 2A, 2B, and 2C can also be configured to take in power from a commercial power source without incorporating the battery 33.

EXPLANATION OF REFERENCES 1, 1A, 1B, 1C: ultrasound probe
2, 2A, 2B, 2C: apparatus main body
11: oscillator array
12: probe side wireless communication circuit
13, 13C: probe controller
14, 14C: probe side processor
15, 33: battery
16: probe sensor
21: reception circuit
22: image generation unit
23: imaging unit
24: display controller
25: monitor
26: touch sensor
27: operation panel
28: image memory
29: probe use determination unit
30, 30B: power saving control circuit
31, 31A, 31B, 31C: main body controller
32, 32A, 32B, 32C: main body side processor
41: pulsar
42: amplification unit
43: AD conversion unit
44: beam former
51: signal processing unit
52 DSC
53: image processing unit
G1, G2, G3: ultrasound image

What is claimed is:
1. An ultrasound diagnostic apparatus comprising:
an ultrasound probe having an oscillator array;
an apparatus main body connected to the ultrasound probe; and
an operation panel in which a touch sensor is mounted,
wherein the apparatus main body including an apparatus processor and a power saving control processor,
wherein the apparatus processor includes an imaging processor,
wherein the imaging processor
is configured to transmit and receive an ultrasound beam to and from a subject through the oscillator array and generate an ultrasound image on the basis of a reception signal output from the oscillator array,
wherein the apparatus processor
analyzes the ultrasound image to determine whether or not the ultrasound probe is being used, and
wherein the power saving control processor
controls operations of the ultrasound probe and the apparatus main body by selecting one of a normal mode in which the ultrasound probe and the apparatus main body are normally operated or a power saving mode in which power consumption of at least a part of the ultrasound probe and the apparatus main body is reduced, on the basis of a determination result as to whether or not the ultrasound probe is being used and presence or absence of an operation of the operation panel detected by the touch sensor,
wherein the power saving mode includes a first mode in which only power consumption in the imaging processor included in the apparatus main body is reduced and a second mode in which overall power consumption of the ultrasound probe and the apparatus main body is reduced, and
wherein the apparatus processor determines that the ultrasound probe is being used in a case in which the ultrasound image shows that jelly is applied to the ultrasound probe or that the ultrasound probe is not in a midair radiation state, and determines that the ultrasound probe is not being used in a case in which the ultrasound image shows that jelly is not applied to the ultrasound probe and that the ultrasound probe is in the midair radiation state.
2. The ultrasound diagnostic apparatus according to claim 1,
wherein the power saving control processor switches the normal mode to the power saving mode in a case in which it is determined that the ultrasound probe is not being used and the touch sensor detects that the operation panel is not being operated for a predetermined time in the normal mode.

3. The ultrasound diagnostic apparatus according to claim 2,
wherein the power saving control processor switches the power saving mode to the normal mode in a case in which the touch sensor detects that the operation panel is being operated in the power saving mode.

4. The ultrasound diagnostic apparatus according to claim 3,
wherein the ultrasound probe has a probe sensor which detects that the ultrasound probe is gripped by a user, and
the power saving control processor switches the power saving mode to the normal mode in a case in which the probe sensor detects that the ultrasound probe is gripped in the power saving mode.

5. The ultrasound diagnostic apparatus according to claim 2,
wherein the ultrasound probe has a probe sensor which detects that the ultrasound probe is gripped by a user, and
the power saving control processor switches the power saving mode to the normal mode in a case in which the probe sensor detects that the ultrasound probe is gripped in the power saving mode.

6. The ultrasound diagnostic apparatus according to claim 5,
wherein the probe sensor consists of at least one of a pressure sensor, a capacitance sensor, or a temperature sensor mounted in the ultrasound probe.

7. The ultrasound diagnostic apparatus according to claim 1,
wherein the power saving control processor reduces the power consumption of the imaging processor by selecting the first mode in a case in which it is determined that the ultrasound probe is not being used for a predetermined first time.

8. The ultrasound diagnostic apparatus according to claim 7,
wherein the power saving control processor reduces the overall power consumption of the ultrasound probe and the apparatus main body by switching the first mode to the second mode in a case in which the touch sensor detects that the operation panel is not being operated for a predetermined second time in the first mode.

9. The ultrasound diagnostic apparatus according to claim 1,
wherein the operation panel has a monitor and the touch sensor disposed so as to overlap the monitor.

10. The ultrasound diagnostic apparatus according to claim 1,
wherein the power saving control processor switches the power saving mode to the normal mode in a case in which the touch sensor detects that the operation panel is brought into contact in a predetermined first contact pattern in the power saving mode.

11. The ultrasound diagnostic apparatus according to claim 10,
wherein the power saving control processor switches the normal mode to the power saving mode in a case in which the touch sensor detects that the operation panel is brought into contact in a predetermined second contact pattern in the normal mode.

12. The ultrasound diagnostic apparatus according to claim 11,
wherein the first contact pattern and the second contact pattern are the same patterns as each other.

13. A control method for an ultrasound diagnostic apparatus provided with an ultrasound probe having an oscillator array, and an apparatus main body connected to the ultrasound probe, the apparatus main body including an apparatus processor and a power saving control processor, the apparatus processor including an imaging processor, the control method comprising:
transmitting and receiving an ultrasound beam to and from a subject through the oscillator array and generating an ultrasound image on the basis of a reception signal output from the oscillator array with the imaging processor;
analyzing the ultrasound image to determine whether or not the ultrasound probe is being used with the apparatus processor; and
controlling operations of the ultrasound probe and the apparatus main body with the power saving control processor by selecting one of a normal mode in which the ultrasound probe and the apparatus main body are normally operated or a power saving mode in which power consumption of at least a part of the ultrasound probe and the apparatus main body is reduced, on the basis of a determination result as to whether or not the ultrasound probe is being used and the presence or absence of an operation of an operation panel detected with a touch sensor,
wherein the power saving mode includes a first mode in which only power consumption in the imaging processor included in the apparatus main body is reduced and a second mode in which overall power consumption of the ultrasound probe and the apparatus main body is reduced, and
wherein it is determined by the apparatus processor that the ultrasound probe is being used in a case in which the ultrasound image shows that jelly is applied to the ultrasound probe or that the ultrasound probe is not in a midair radiation state, and that the ultrasound probe is not being used in a case in which the ultrasound image shows that jelly is not applied to the ultrasound probe and that the ultrasound probe is in the midair radiation state.

\* \* \* \* \*